United States Patent
Prasad Dasi et al.

(10) Patent No.: US 12,159,720 B2
(45) Date of Patent: Dec. 3, 2024

(54) SYSTEMS AND METHODS FOR OPTIMIZING MEDICAL INTERVENTIONS USING PREDICTIVE MODELS

(71) Applicant: DasiSimulations, LLC, Dublin, OH (US)

(72) Inventors: Lakshmi Prasad Dasi, Dublin, OH (US); Theresa L. Sirset, Rancho Palos Verdes, CA (US)

(73) Assignee: DasiSimulations, LLC, Dublin, OH (US)

( * ) Notice: Subject to any disclaimer, the term of this patent is extended or adjusted under 35 U.S.C. 154(b) by 95 days.

(21) Appl. No.: 17/805,606

(22) Filed: Jun. 6, 2022

(65) Prior Publication Data
US 2022/0392642 A1  Dec. 8, 2022

Related U.S. Application Data

(60) Provisional application No. 63/197,807, filed on Jun. 7, 2021.

(51) Int. Cl.
*G16H 50/20* (2018.01)
*G16H 10/60* (2018.01)
*G16H 50/70* (2018.01)
*G16H 70/20* (2018.01)

(52) U.S. Cl.
CPC ............ *G16H 50/20* (2018.01); *G16H 10/60* (2018.01); *G16H 50/70* (2018.01); *G16H 70/20* (2018.01)

(58) Field of Classification Search
CPC ........ G16H 50/20; G16H 10/60; G16H 50/70; G16H 70/20
See application file for complete search history.

(56) References Cited

U.S. PATENT DOCUMENTS

| 8,435,964 B2 * | 5/2013 | Mathieu | C12Q 1/42 514/47 |
| 8,663,318 B2 * | 3/2014 | Ho | A61F 2/2433 623/2.11 |

(Continued)

OTHER PUBLICATIONS

Hosny, 2019, Elsevier, pp. 21-30.*

(Continued)

*Primary Examiner* — Michael I Ezewoko
(74) *Attorney, Agent, or Firm* — Benesch Friedlander Coplan & Aronoff LLP (57) ABSTRACT

A computer implemented method for prescribing optimized medical interventions includes retrieving a patient's updated electronic medical record (EMR) and mapping the diagnosis of the patient to a medical treatment database to select a plurality of likely medical intervention choices based on a score exceeding a defined threshold score. The method includes determining a rank order of the selected plurality of medical intervention choices by comparing simulation outcomes for each choice executed by the medical predictive algorithm, on respective choices among each of the selected likely medical interventions. The method also includes receiving by the patient's physician or patient's electronic medical record database, a rank order of recommended medical intervention choices including possible options and associated metrics based on an accepted level of simulated outcome.

20 Claims, 3 Drawing Sheets

(56) References Cited

U.S. PATENT DOCUMENTS

| | | | | |
|---|---|---|---|---|
| 8,663,319 | B2* | 3/2014 | Ho | A61B 17/12122 623/2.11 |
| 9,216,076 | B2* | 12/2015 | Mitra | A61L 31/048 |
| 9,259,202 | B2* | 2/2016 | Yoshida | A61B 6/503 |
| 9,308,086 | B2* | 4/2016 | Ho | A61F 2/2427 |
| 9,468,458 | B2* | 10/2016 | McDonald | A61B 17/320758 |
| 9,480,564 | B2* | 11/2016 | Ho | A61F 2/2418 |
| 9,566,178 | B2* | 2/2017 | Cartledge | A61F 2/966 |
| 9,592,111 | B2* | 3/2017 | Groh | A61F 2/2427 |
| 9,619,614 | B2* | 4/2017 | Rodriguez | H04L 63/08 |
| 9,652,862 | B1* | 5/2017 | Speidel | G06T 7/344 |
| 9,700,410 | B2* | 7/2017 | Ho | A61B 17/1204 |
| 9,727,829 | B2* | 8/2017 | Bollapragada | G06Q 10/0631 |
| 9,801,716 | B2* | 10/2017 | Pollack | A61B 90/37 |
| 9,814,611 | B2* | 11/2017 | Cartledge | A61F 2/93 |
| 9,827,093 | B2* | 11/2017 | Cartledge | A61B 5/6862 |
| 9,855,143 | B2* | 1/2018 | Ho | A61F 2/2454 |
| 9,861,464 | B2* | 1/2018 | Azimpour | A61F 2/013 |
| 9,889,006 | B2* | 2/2018 | Sandhu | A61F 2/2427 |
| 9,913,716 | B2* | 3/2018 | Cartledge | A61F 2/2418 |
| 10,043,267 | B2* | 8/2018 | Yamamori | G06T 7/0012 |
| 10,080,654 | B2* | 9/2018 | Ho | A61B 17/12136 |
| 10,098,644 | B2* | 10/2018 | Ho | A61B 17/12136 |
| 10,220,192 | B2* | 3/2019 | Drasler | A61B 90/39 |
| 10,226,333 | B2* | 3/2019 | Al-Jilaihawi | A61F 2/2412 |
| 10,238,514 | B2* | 3/2019 | Cartledge | A61F 2/844 |
| 10,327,898 | B2* | 6/2019 | Groh | A61F 2/2427 |
| 10,335,276 | B2* | 7/2019 | McDonald | A61F 2/2496 |
| 10,405,817 | B2* | 9/2019 | Wakai | A61B 6/54 |
| 10,463,259 | B2* | 11/2019 | Glover | A61B 5/02055 |
| 10,478,295 | B2* | 11/2019 | Cartledge | A61F 2/2418 |
| 10,507,301 | B2* | 12/2019 | Al-Jilaihawi | A61M 25/0071 |
| 10,531,851 | B2* | 1/2020 | Wilson | A61B 6/5217 |
| 10,543,078 | B2* | 1/2020 | Al-Jilaihawi | A61F 2/2427 |
| 10,561,488 | B2* | 2/2020 | Groh | A61F 2/013 |
| 10,629,096 | B2* | 4/2020 | Kheradvar | G09B 23/30 |
| 10,704,093 | B2* | 7/2020 | Deng | C12Q 1/6876 |
| 10,709,558 | B2* | 7/2020 | Sandhu | A61M 25/04 |
| 10,726,742 | B2* | 7/2020 | Wang | B33Y 80/00 |
| 10,751,181 | B2* | 8/2020 | Ho | A61F 2/2412 |
| 10,765,888 | B2* | 9/2020 | Sjolund | A61N 5/1038 |
| 10,789,772 | B2* | 9/2020 | Mortier | G06T 17/20 |
| 10,820,989 | B2* | 11/2020 | Al-Jilaihawi | A61F 2/2418 |
| 10,864,009 | B2* | 12/2020 | McDonald | A61M 29/00 |
| 10,869,756 | B2* | 12/2020 | Al-Jilaihawi | A61F 2/2436 |
| 10,874,508 | B2* | 12/2020 | Cartledge | A61F 2/2439 |
| 10,881,412 | B2* | 1/2021 | Ho | A61F 2/2427 |
| 10,888,297 | B2* | 1/2021 | McDonald | A61B 6/481 |
| 10,926,068 | B2* | 2/2021 | Narayan | A61M 60/865 |
| 10,937,337 | B2* | 3/2021 | Okayama | G09B 23/34 |
| 10,953,194 | B2* | 3/2021 | Ramanathan | A61M 25/0136 |
| 10,960,177 | B2* | 3/2021 | Ramanathan | A61M 25/0097 |
| 10,980,650 | B2* | 4/2021 | Cartledge | A61F 2/82 |
| 11,008,381 | B2* | 5/2021 | Witztum | A01K 67/0275 |
| 11,008,382 | B2* | 5/2021 | Witztum | A01K 67/0275 |
| 11,045,256 | B2* | 6/2021 | Mortier | A61B 5/026 |
| 11,051,885 | B2* | 7/2021 | Mortier | A61B 5/026 |
| 11,065,110 | B2* | 7/2021 | Bianco | A61B 6/12 |
| 11,069,136 | B2* | 7/2021 | Mortier | G06T 17/20 |
| 11,071,844 | B2* | 7/2021 | Merhi | A61F 2/013 |
| 11,141,220 | B2* | 10/2021 | Mortier | G16H 50/50 |
| 11,166,803 | B2* | 11/2021 | McGowan | A61F 2/013 |
| 11,191,640 | B2* | 12/2021 | Groh | A61F 2/013 |
| 11,197,619 | B2* | 12/2021 | Glover | G01K 13/02 |
| 11,197,754 | B2* | 12/2021 | Saffari | A61F 2/2418 |
| 11,213,253 | B2* | 1/2022 | Kassab | A61B 5/1076 |
| 11,253,356 | B2* | 2/2022 | Ho | A61B 17/12136 |
| 11,259,767 | B2* | 3/2022 | Garg | G16H 50/30 |
| 11,272,847 | B2* | 3/2022 | Glover | A61B 5/6853 |
| 11,273,038 | B2* | 3/2022 | Tang | A61F 2/9517 |
| 11,284,849 | B2* | 3/2022 | Wilson | G16H 50/30 |
| 11,328,416 | B2* | 5/2022 | Zareian | A61B 6/032 |
| 11,331,149 | B2* | 5/2022 | Mortier | G16H 30/20 |
| 11,337,798 | B2* | 5/2022 | Azadani | A61F 2/2412 |
| 11,342,080 | B2* | 5/2022 | Sharma | G16H 50/30 |
| 11,364,118 | B2* | 6/2022 | Kheradvar | A61F 2/2427 |
| 11,382,694 | B2* | 7/2022 | Dasi | A61B 5/0044 |
| 11,406,271 | B2* | 8/2022 | Glawdel | A61F 2/2427 |
| 11,464,639 | B2* | 10/2022 | Silberbach | A61B 34/10 |
| 11,471,657 | B1* | 10/2022 | Busiashvili | A61M 35/10 |
| 11,478,346 | B2* | 10/2022 | Groh | A61F 2/0105 |
| 11,512,351 | B2* | 11/2022 | Deng | C12Q 1/6883 |
| 11,583,355 | B2* | 2/2023 | Sadan | A61F 2/013 |
| 11,612,730 | B1* | 3/2023 | Lin | A61M 5/14 600/424 |
| 11,626,212 | B2* | 4/2023 | Crawford | G06T 7/11 345/423 |
| 11,647,942 | B1* | 5/2023 | Busiashvili | G16H 50/20 604/890.1 |
| 11,648,414 | B2* | 5/2023 | Ramaswamy | A61N 2/004 600/14 |
| 11,655,288 | B2* | 5/2023 | Witztum | A01K 67/0275 536/23.53 |
| 11,663,929 | B2* | 5/2023 | Okayama | G09B 23/303 434/268 |
| 11,668,721 | B2* | 6/2023 | Ferrari | G01N 33/6893 600/407 |
| 11,707,356 | B2* | 7/2023 | Cartledge | A61F 2/95 623/2.11 |
| 11,717,390 | B2* | 8/2023 | Merhi | A61B 17/00234 606/200 |
| 11,752,122 | B2* | 9/2023 | Ahamed | A61K 31/198 514/562 |
| 11,759,315 | B1* | 9/2023 | Fischell | A61F 2/24 623/2.1 |
| 11,766,328 | B1* | 9/2023 | Fischell | A61N 1/37 623/2.11 |
| 11,779,776 | B2* | 10/2023 | Ramaswamy | A61N 2/02 600/14 |
| 11,786,354 | B2* | 10/2023 | Vardi | A61F 2/013 606/200 |
| 11,826,253 | B2* | 11/2023 | Ho | A61F 2/2466 |
| 11,833,042 | B2* | 12/2023 | Sandhu | A61F 2/2427 |
| 11,844,645 | B2* | 12/2023 | Motamed | A61B 8/488 |
| 11,849,910 | B2* | 12/2023 | Leonhardt | A61F 2/2409 |
| 11,864,994 | B2* | 1/2024 | Li | A61F 2/2436 |
| 11,869,670 | B2* | 1/2024 | Crawford | G06T 15/04 |
| 11,877,927 | B2* | 1/2024 | Lyer | A61F 2/2418 |
| 11,883,286 | B2* | 1/2024 | Quill | A61F 2/2418 |
| 2018/0311510 | A1 | 11/2018 | Sjolund et al. | |
| 2019/0065687 | A1 | 2/2019 | Mei et al. | |
| 2019/0298450 | A1* | 10/2019 | Dasi | G16H 50/50 |
| 2020/0152307 | A1 | 4/2020 | Ambrose et al. | |
| 2021/0134415 | A1 | 5/2021 | Soto et al. | |
| 2021/0346097 | A1 | 11/2021 | Dasi et al. | |

OTHER PUBLICATIONS

Khan, May 2021, Elsevier, pp. 941-948.*
Shinbane, 2018, Elsevier, pp. 16-27.*
Webb, 2012, Elsevier, pp. 520-528.*
International Search Report and Written Opinion issued in PCT application No. PCT/US2022/072784, mailing date Aug. 19, 2022.

* cited by examiner

SYSTEMS AND METHODS FOR OPTIMIZING MEDICAL INTERVENTIONS USING PREDICTIVE MODELS

CROSS REFERENCE OF RELATED APPLICATION

This application claims priority to U.S. Provisional Patent Application No. 63/197,807 filed Jun. 7, 2021, which is incorporated herein by reference in entirety.

FIELD

The present disclosure generally relates to systems and methods for optimizing medical interventions using predictive models, more specifically, for optimizing medical therapy decisions based on predictive models based guidelines.

BACKGROUND

Medical therapies involve decisions made by clinicians such as doctors when evaluating a patient. It is no surprise that a wrong decision made by a doctor may mean life or death for the patient. Wrong (or sub-optimal) decisions may include failure to diagnose or mis-diagnosis, or picking a treatment plan option out of multiple options available that may lead the patient and the doctor down a path leading to sub optimal outcomes. The primary stakeholder is the patient who is hoping to maximize life expectancy and quality of life (for a specified cost or minimal costs or affordable costs). The secondary stakeholder is the treating clinician and the institution/hospital who is hoping to ethically maximize profit and reputation.

While for many years medical societies have provided, written, and updated treatment guidelines for almost every prevalent disease based on population level experience from each prevalent disease, or when there is new promising and effective treatments that become available, it is well known that these guidelines may not necessarily provide the optimal outcome for every individual patients. Typically, treatment options provided in these guidelines may include shared decision making involving the patient into the decision making process. Because the population derived guidelines are routinely in current medical practice may not take into account all the details of the patient's specific genetic, biological, anatomical, and/or physiological characteristics, following the guidelines which may not guarantee the most optimal outcome for individual patients.

SUMMARY

A computer implemented method for prescribing optimized medical interventions, includes executing by at least one processor in a server, a medical predictive algorithm stored in a memory for prescribing an optimized medical intervention according to a diagnosis.

A system for prescribing optimized medical interventions, includes at least one processor in a server executing a medical predictive algorithm stored in a memory for prescribing an optimized medical intervention according to a diagnosis.

A non-transitory computer-readable medium having stored in a memory, program code of a medical predictive algorithm, when executed by at least one processor of a machine, the medical predictive algorithm causes the machine to carry out steps for prescribing optimized medical interventions.

The prescribing of the optimized medical intervention includes retrieving from a patients database, a patient's updated electronic medical record (EMR) including at least two or more of: patient's demographic data, morbid symptoms, vital signs, medications, surgery history, family medical history, genetic data, laboratory test data, diseases records, allergies, X-ray images or computer generated tomography images, and medical insurance information.

The prescribing of the optimized medical intervention incudes mapping the diagnosis of the patient to a medical treatment database to select a plurality of likely medical intervention choices based on a score exceeding a defined threshold score. The score is a linear or non-linear combination of individual scores assigned to each of a plurality of objective functions including at least one or more of: treatment duration, total treatment cost, risk factor of treatment, projected life expectancy of treatment, success rate of treatment, rehabilitation duration, out-patient rehabilitation cost, quality of life index after treatment, implant device useful life, facilities rating and reimbursable cost from insurance carrier.

The prescribing of the optimized medical intervention includes determining a rank order of the selected plurality of medical intervention choices by comparing simulation outcomes for each choice executed by the medical predictive algorithm, on respective choices among each of the selected likely medical interventions. The prescribing of the optimized medical intervention includes receiving by the patient's physician or patient's electronic medical record database, a rank order of recommended medical intervention choices including possible options and associated metrics based on an accepted level of simulated outcome.

DETAILED DESCRIPTION

The present disclosure provides an additional step to individualize the population derived guideline by taking into account patient specific information that may be predictive of known risks for a treatment options available to the patient. The advent of predictive models using some combination of artificial intelligence, machine learning, big-data, and computational simulations brings the possibility of being able to predict with some certainty (or uncertainty) the time course of what may happen to a patient when and if these models begin taking into account patient's specific genetic, biological, anatomical, and/or physiological characteristics.

The disclosure here may be a system to optimize the decision making for structural heart treatment such as valve repair and replacement. A person of skill in the art may recognize that the system may also be configured to work with other cardiac or non-cardiac surgical treatment involving a surgical or catheter based intervention including robotic surgery or interventions.

The system may also be generalized to treat any disease where a plurality of treatment options exist.

For example, transcatheter valve repair or replacement (TVR) for aortic, mitral, pulmonary, and tricuspid valves may provide treatment for patients with severe valve disease, and high-risk patients with various comorbidities, who cannot undergo conventional open-heart surgery. Despite the advantages associated with TVR, complications such as, for example, conduction abnormalities, significant residual regurgitation or leakage, tissue rupture, valve thrombosis, valve embolization, and flow obstruction and other cerebrovascular events can still occur. The complication events may include coronary obstruction, paravalvular leakage, and thrombosis. Other complications include those that may risk of several adverse outcomes that may happen at the time of surgery or even months after surgery (e.g., valve thrombosis). Furthermore, these models may also be used to predict the future risks of interventions when the current intervention device fails (e.g., future valve in valve or TAVR inside TAVR procedures). Examples of these models may be found in U.S. Patent Application Publication No. 2019/0298450, entitled "SYSTEMS AND METHODS FOR PREDICTIVE HEART VALVE SIMULATION," which using a parametric analysis engine to model a gap size $\alpha_{2D}$ distance in TAV stent deployment, which the gap size $\alpha_{2D}$ distance between the tip of the coronary leaflet and coronary ostium of the coronary artery may be correlated to risk of coronary obstruction. A summary of the clinical statuses for several patients using gap sizes $\alpha_{2D}$ with coronary obstruction risk level are tabulated in Table1 below.

TABLE 1

| Patients # | $\alpha_{2D}$ for Left Coronary Ostium (mm) | $\alpha_{2D}$ for Right Coronary Ostium (mm) | $\alpha_{3D}$ for Left Coronary Ostium (mm) | $\alpha_{3D}$ for Right Coronary Ostium (mm) | Coronary Obstruction Risk Level | TAVR Operation Completed | Coronary Obstruction Confirmation |
|---|---|---|---|---|---|---|---|
| A | 14.78 | 7.52 | 12.38 | 7.4 | low | Yes | No |
| B | 3.53 | 3.62 | 2.58 | 3.39 | low | Yes | No |
| C | 8.69 | 5.96 | 6.68 | 7.07 | low | Yes | No |
| D | 3.87 | 2.26 | 4.6 | 2.54 | moderate | Yes | No |
| E | 0.98 | 5.69 | 0.93 | 6.4 | high | No | n/a |
| F | 2.16 | 2.24 | 0.85 | 3.13 | high | No | n/a |
| G | 0.60 | 4.24 | 0.7 | 7.46 | high | Yes | Yes |
| H | 7.50 | 6.85 | 5.99 | 6.33 | low | Yes | Yes |
| I | 0 | 0 | 0 | 0 | high | Yes | Yes | occur from the delivery process such as vascular injury, or inability of the delivery catheter to navigate a narrowing in the vasculature. The decision for a patient to undergo TVR as opposed to more invasive procedures such as open heart surgery is complex and may depend on a multitude of factors. These factors include the age, sex medical conditions, frailty, their Society of Thoracic Surgeons (STS) risk score, prior history related to structural heart procedures, complexity of the delivery route from the catheter, ability of the patient to recover from an open heart surgery and so on.

Current guidelines by the American heart association and American college of cardiology or other societies recommending treatment strategies for heart valve repair and replacement may purely rely on population based risk assessment ignoring relevant patient specific factors such as genetic, biological, anatomical, and/or physiological characteristics of the lesion or multiple mixed lesions afflicting the various cardiac structures. Risk calculators are often used such as the STS Predicted Risk of Mortality (PROM) score but these calculators do not take into account the genetic, biological, anatomical, and/or physiological characteristics of the lesion or mixed lesions. Risk calculators are typically built on statistical models based on national registry data compiled across all the sites performing specific procedures. The prediction capacity is limited to the parameters recorded which typically only involve general parameters such as age, sex, and other medical factors such as co-morbidities, basic vital and metabolic parameters (e.g., kidney function, lung function etc.). Detailed anatomical information are usually not included in these models.

In an example, computational models may be made available to simulate the transcather valve replacement or repair procedure and holds the potential for assessing the These simulations may involve starting with 3D model generation from medical images of the patient followed by subjecting the 3D models to simulation of TAV using computational frameworks that can predict the structural response as well as the hemodynamic performance and other flow parameters and flow patterns. Therefore it would now be possible to individualize the previously developed risk scores by adding individual level predictions into the calculation. With a new risk calculator that combines population based prediction with individualized simulation to predict specific adverse outcomes (of current and future interventions) will yield more accurate risk calculation at an individual level to optimize the decision making. The more individualized imaging, genetic, or physiological data included in the individualized prediction of adverse outcomes, the more accurate the combined model will become at predicting individualized risk for a given medical treatment or intervention.

While it may be useful to have computer simulations to screen for individual adverse outcomes, the optimal decision for the patient needs to involve a more holistic picture where all options (invasive treatment vs transcatheter treatment vs medical management) are considered. For each option considered it is important to identify the risk of various adverse outcomes happening along with the potential implications of that adverse outcome for patient as well as the treating center (e.g., hospital). For the patient the implications deal with expected lifespan, quality of life, and costs. For the hospitals the implications are changes in patients length of stay and additional costs that will be incurred by the hospital and reputation. In addition to considering these implications, another set of implications for the patient is that each decision can set the stage for other decisions to be made in the future. For example, if a decision is being considered to implant a prosthetic valve now, then it should also be anticipated that the patient will need another valve within about 10 years. Furthermore, if the patient will require coronary interventions in the future (based on prognosis of coronary artery disease) then the access to the coronaries must also be factored into the current decision depending on how advanced coronary artery disease is in the patient as observed from the Computerized Tomography (CT) scan images.

This type of holistic view maps out the early decisions from the doctors or by the heart team group to the outcomes for both the patient and the hospital. As an example, the decision to treat a younger low risk patient (based on STS score alone) with TVR as opposed to open heart surgery could mean the certainty of future interventions such as additional transcatheter or open heart surgeries in the future. The analogy is the game of chess, where the player who can account for future moves and counter moves has a better probability of winning. Similarly, a medical decision support system that lays out all the implications from each decision point in a quantitative manner in order to select the best decision path for the best outcome is critical. Such an optimal decision cannot be made without a systems level planning and intelligence driven guideline system. As described above, such a system collects nearly real time data from all the centers, which updates population based predictive models with ever increasing precision to include genetic, anatomic, and other physiological parameters into the data collection. The system also consists of simulation capability to simulate the biomechanical interaction of devices within the patient while considering all possible treatment options (current and predicted interventions in the future) and then calculate a precise risk score for each treatment path. The system may be configured to visually interactive display (e.g., touch screen device, or virtual reality display device, or augmented reality device) the decision tree or map and highlight the most optimal decision path or paths for each of the optimization variable (e.g., cost, patient lifespan, etc.). Such a system will serve as the intelligence and present best options with justifications for the clinician to discuss with the team and the patient and family to execute a collectively chosen treatment plan. Such a system that can be centrally executed using a service or cloud computing platform is the subject of the present disclosure. Furthermore, every patient may install an app on their personal device that is connected to the system will display the patient's life expectancy in real time which may be updated with every change in the patients electronic medical record. Furthermore, the app may also be connected to wearable sensors that may also feed updated biological, physiological, cognitive, mental, and other biomarker data which will also be used into the system's predictive algorithms. Apps such as those will be useful as the patients can adjust their lifestyle to maximize their life expectancy and quality of life.

In this disclosure, machine learning and/or artificial neural network or deep learning algorithms are trained and updated at regular intervals of time to track patient healthcare parameters and outcomes such as length of stay, cost of care, itemized list of supplies used during care (sticks, saline bags, accessories etc.), valve durability, life expectancy, and probability of complications at national, regional, down to center/hospital specific level. For example, the machine learning algorithm will be able to predict length of stay, costs, and projected lifespan for a patient who underwent TAVR and resulted in the placement of a permanent pacemaker. These algorithms may be trained on retrospective data from all medical data available for a patient who underwent structural heart procedures such as open heart surgery or trans-catheter procedures.

These AI/ML algorithms are then coupled with computational predictive models to form a systems optimization approach or software to model all possible options current and future spanning every possible time course for the patient. For example, a patient diagnosed with aortic stenosis will be run with all options such as open heart surgery or trans-catheter valve replacement. For each option computational simulations will predict the risks of adverse outcomes happening with each device available for the option. The computational simulations may include Monte-Carlo simulations to incorporate uncertainties during the deployment of the devices to predict probabilities of adverse outcomes. For each device chosen the future valve in valve device simulation will also be conducted in a similar manner. Simulations may also include predicted remodeling of the cardiac structures (as learned from AI/ML training from the data collection) and similarly predicted increase in other structural heart diseases such as coronary artery disease. The AI/ML algorithms will predict healthcare implications for both the patient and hospital for each decision tree/path including the expected life span, cost, and quality of life index for each decision path. This concept may be depicted in FIGS. 1A and 1B.

Figure 1A:
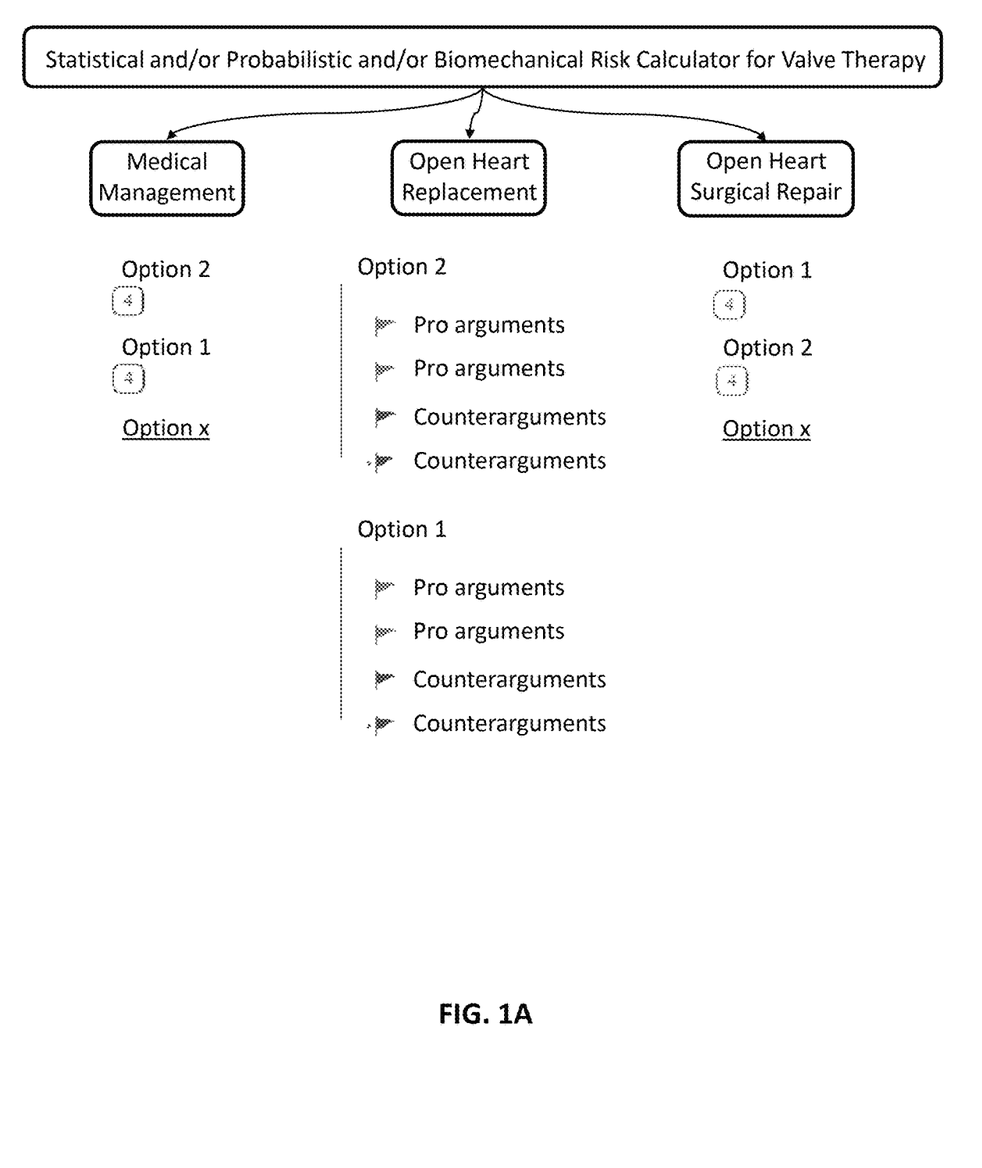
FIGS. 1A and 1B show an example illustration of using Artificial Intelligence/Machine Learning (AI/ML) algorithms to predict healthcare implications for both the patient and hospital for each decision tree/path including the expected life span, cost, and quality of life index for each decision path.
Figure 1B:
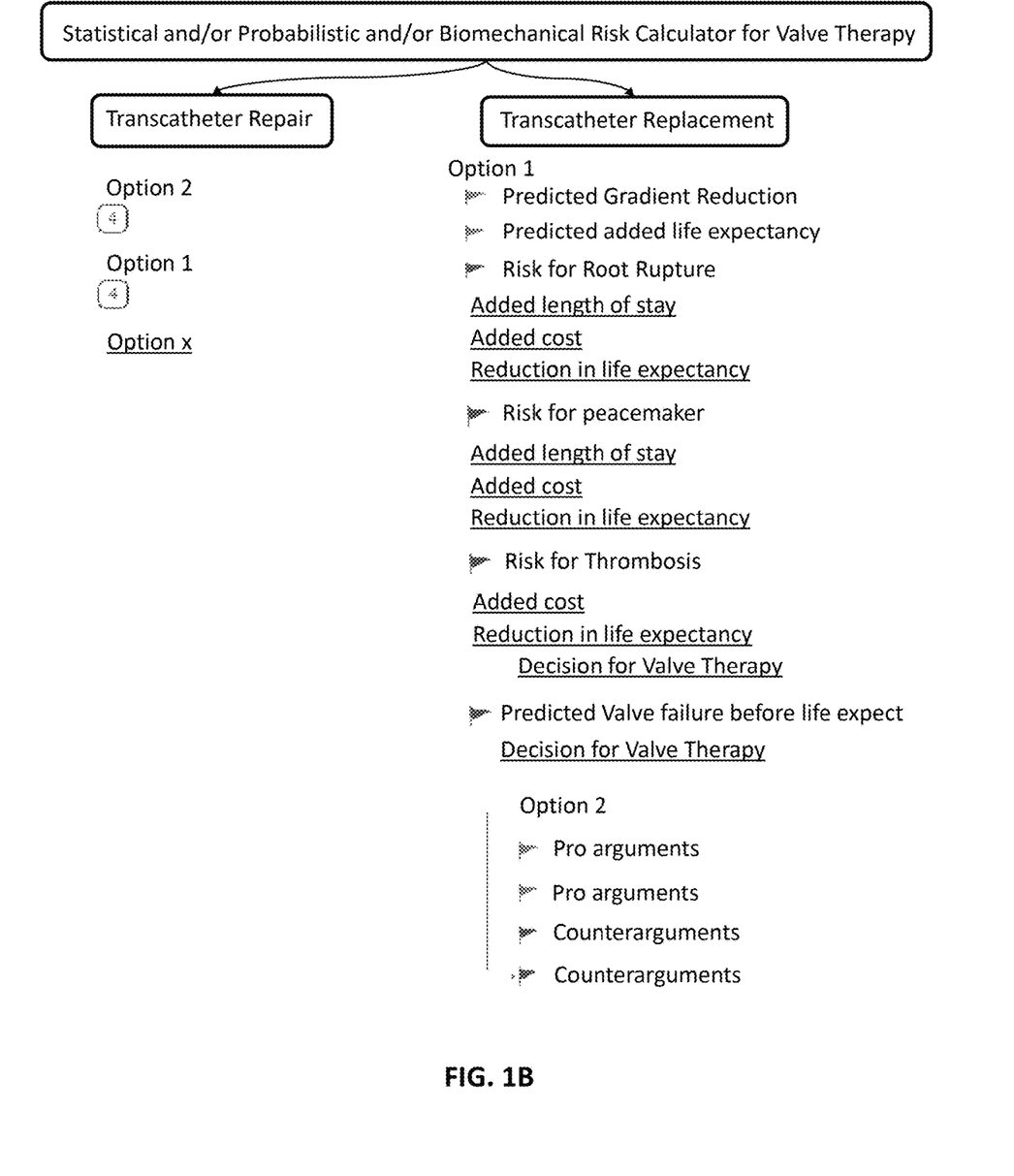

The system can display the decision paths as a visual map highlighting best and worst paths including intermediate paths. Clicking on a path will display life expectancy, cost, quality of life, as well as parameters for interest to the hospital such as potential cost savings and profitability.

Figure 2:
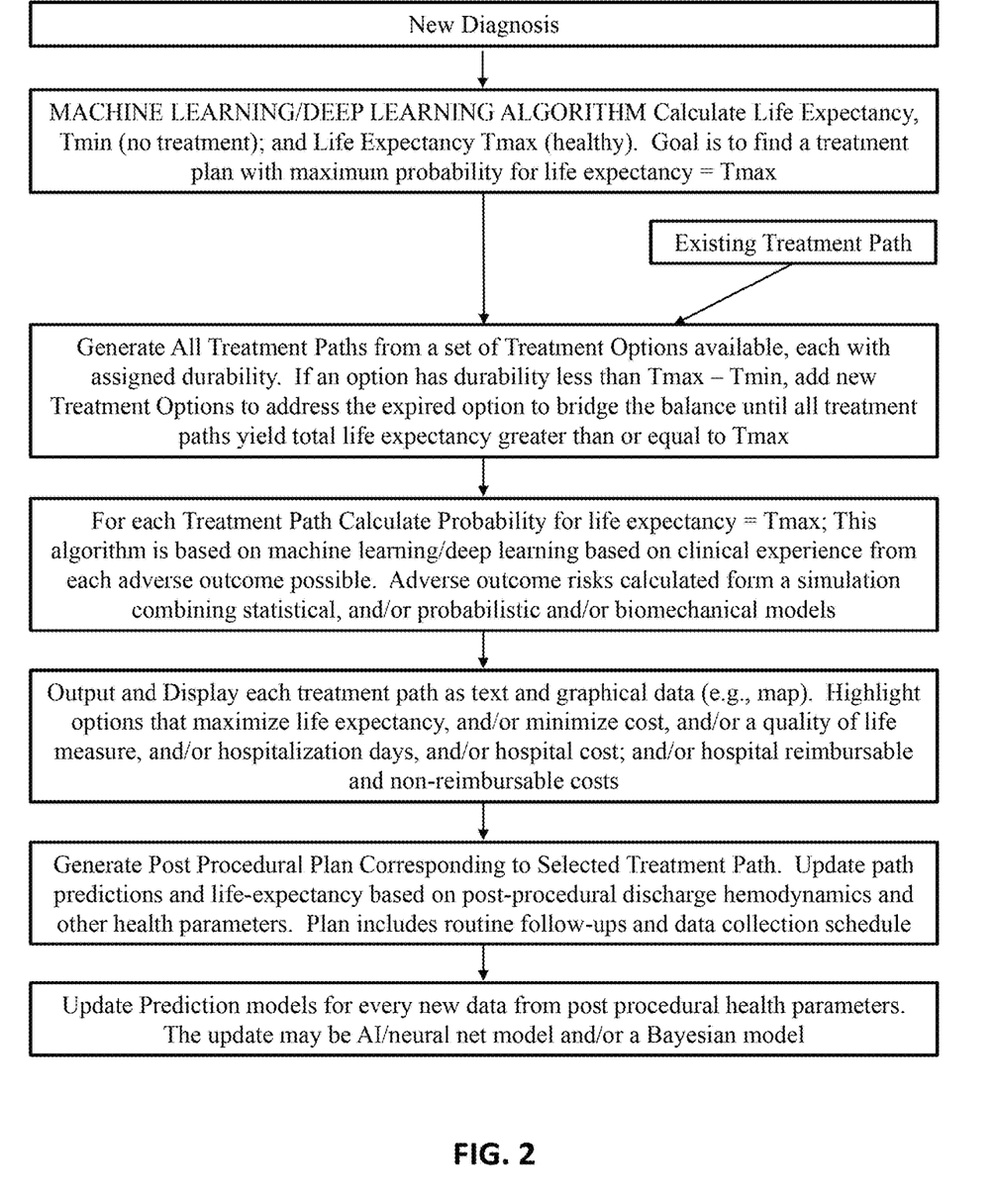
FIG. 2 shows an example method of using artificial intelligence driven guideline system to develop an optimal treatment path for a patient needing a replacement heart valve.

FIG. 2 shows some examples of the executed steps of the artificial intelligence driven guideline system. Specifically, FIG. 2 illustrates the building of an optimization system with an example of developing an optimal treatment path for a patient needing replacement heart valve.

In an example, a patient in her 50s came in with Aortic Stenosis with an existing bioprosthetic valve that had been calcified. An (Artificial Neural Network) ANN model with minimum of one layer and minimum of one neuron is trained to output life expectancy of individuals based on current health status. The training dataset may contain a database of electronic medical history of patients including medical health parameters such as various conditions and the severity of each condition. The dataset preferably may span over the maximum extent possible preferably over ten years. The model may be trained every week after new data is synchronized with participating medical institutions. The model may not require any personal identifiers. However, the model may include relevant information including genetic, race, gender, geographic location, and relevant vital functional status of kidneys, lungs, liver, blood cholesterol etc. Family history and all past diagnosis and their treatment status. The ANN model may output the life-expectancy in terms of predicted age at death as well as number of years left to live. The model may also output life-expectancy if the status of the disease in question is hidden from the model. This may mean that the model may assume an absence of the current disease and output of what may be a life-expectancy in an absence of a new diagnosis.

This trained predictive life-expectancy model may predict to be only one year if untreated. The algorithm may also predict a life-expectancy for the same patient absent of aortic stenosis at 85 years. The system may recognize that the potential best case scenario of developing a treatment path is to try to add 34 years back to the expected life expectancy. The system may set a goal as to pick a treatment path that will bring a life-expectancy from 51 years to 85 years (or adding 34 additional years of expectancy).

The system has another ANN model trained to output how long a valve would last before it fails. This model is a similar ANN model as previously described and is trained on medical records consisting of all patients who received a replacement valve. The model may be trained to output a predicted usable life of every valve in the market based on the patient's age, and all vital parameters including but not limited to renal function.

For an example of a patient, the model may estimate a new Sapien valve available from Edwards Lifesciences (hereinafter "Sapien") to last for 10 years, while a new Evolut valve (e.g., Medtronic Evolut™ TAVR; hereinafter "Evolut") may last for 6 years. The model also may estimate 16 years for a new Carpentier Edwards Perimount valve (hereinafter "Perimount"), 14 years for Magna valve, and 12 years for Mitroflow (e.g., Mitroflow aortic valve).

A next step in the system may be a treatment path generator. This may be an algorithm that takes into account the available options and lays out all possible treatment paths including the path of medical management alone. These treatment paths may also be referred to as medical intervention. The algorithm ensures that the treatment paths or medical intervention choices are laid out such that the total combined usable life of the devices in the path may sum to greater than the patient's maximum possible life expectancy. The medical intervention may also include variations such as different depth of implantation for valves, different sizing (oversizing or under-sizing by set amounts), different angles of deployment from variations in how the guidewire may place the implant in the aortic root etc.

In an example, the following medical intervention choices may be generated:

Choice No. 1: Medical management.
Choice No. 2: Open heart valve replacement with Perimount followed by Open heart valve replacement with Perimount followed by Open heart valve replacement with Perimount=total usable life 16+16+16=48 years.
Choice No. 3: Open heart valve replacement with Perimount followed by TAVR Valve-in-Valve (ViV) replacement with Evolut followed by Valve-in-Valve-in-Valve (ViViV) with Sapien=total usable life 16+6+10=32 years.

All of the medical intervention may then passed on to the next algorithm. The next algorithm may evaluate overall probability of life expectancy of greater than or equal to 34 years for each medical intervention and sorts the choices from maximum probability to the minimum probability.

This algorithm may include information from training based on data from participating institutions/hospitals etc., which may be updated every time new data is available. The algorithm with pre-calculated probability distribution function of life expectancy after open heart surgery may be conditioned on the selected valves, geographic location, age of patient at time of surgery, co-morbidities, and other medical information (current and projected for the future) of the patient. Another condition is that no adverse outcome occurred.

The algorithm with pre-calculated probability distribution function of life expectancy after trans-catheter valve replacement conditioned on the selected valves, geographic location, age at time of surgery, co-morbidities, and other medical information (current and projected for the future) of the patient etc. Another condition is that no adverse outcome occurred.

The algorithm with pre-calculated probability distribution functions of life expectancy conditioned for each adverse outcome (and any combination) may occur due to at least the following reasons: root rupture; paravalvular leakage level; patient prosthesis mismatch; valve thrombosis; coronary obstruction; valve embolization; placement of permanent pacemaker; stroke; combinations (e.g., patient prosthesis mismatch+valve thrombosis); and other.

The algorithm may compute a probability of each adverse outcome occurring at each procedure in the treatment path by running biomechanical predictive simulations based on the patient's medical images. Each treatment path may be simulated. The biomechanical predictive models may include an algorithm that may be used to (1) predict likelihood of thrombosis after transcatheter aortic valve (TAV) replacement (TAVR) based on valve and patient specific anatomic and hemodynamic parameters and (2) select an optimal valve and placement for individual patients for minimization of the likelihood of thrombosis. The algorithm may be designed to incorporate valve and patient-specific parameters with a class of empirical and semi-empirical modeling to rapidly predict areas of flow stasis or the magnitude of flow stasis that are likely to lead to blood clot formation in the vicinity of the artificial valve, then outputs the probability of each adverse outcome occurring at each stage in the treatment paths.

The algorithm may run a Monte-Carlo simulation for each medical intervention given the individual probabilities of each adverse outcomes occurring in each treatment path using the probability density functions and the conditional probability density functions to compute the total probability function of life expectancy for each treatment path. These Monte-Carlo type simulations may be driven by random number generators following the given probability density functions and the probabilities.

The algorithm may use the final probability density function to estimate a probability of life expectancy greater than or equal to 34 years. For the example, the model may output the medical intervention in an order of maximum probability to minimum probability.

Another algorithm may display a length of stay, predicted hospital cost, reimbursable and non-reimbursable costs for each treatment path. This algorithm may be an ANN model that has been trained on data from participating hospitals etc., that may include length of stay and cost information.

What have been described above are examples. It is, of course, not possible to describe every conceivable combination of components or methods, but one of ordinary skill in the art will recognize that many further combinations and permutations are possible. Accordingly, the disclosure is intended to embrace all such alterations, modifications, and variations that fall within the scope of this application, including the appended claims. Additionally, where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on.

The invention claimed is:

1. A computer implemented method for prescribing optimal treatment paths, comprising:
retrieving data relevant to a diagnosis of a disease, the data comprising a patient's updated electronic medical record (EMR) comprising medical images and at least one of: the patient's demographic data, morbid symptoms, vital signs, medications, surgery history, family medical history, genetic data, laboratory test data, diseases records, and allergies;

identifying treatment path options based on selections made by medical professional personnel or according to guidelines generated by medical societies, wherein the treatment path options comprise at least one surgical treatment or intervention;

using a trained predictive life-expectancy model to predict a life expectancy for each of the treatment path options based on the data and probability distribution functions conditioned on adverse outcomes of the at least one surgical treatment or intervention, wherein the adverse outcomes are generated by predictive models comprising a biomechanical model based on the medical images;

performing Monte-Carlo simulations using the probability distribution functions of the adverse outcomes to calculate a total probability function of the life expectancy for each of the treatment path options; and interactively displaying a decision tree to the medical professional personnel and the patient, the decision tree comprising the treatment path options and corresponding total probability functions of the life expectancies, presenting real time predicted life expectancies, sorting the life expectancies from a maximum probability to a minimum probability, and presenting the life expectancies and temporal and monetary costs for each of the treatment path options.

2. The computer implemented method of claim 1, wherein the predictive models further comprise one or more of a trained artificial neural net model, a statistical model, a reduced order model, a semi-empirical, and an empirical model.

3. The computer implemented method of claim 1, wherein the probability distribution functions comprise individual probabilities of each of the adverse outcomes and pre-calculated probability distribution functions of life expectancy after each of the at least one surgical treatment or intervention.

4. The computer implemented method of claim 1, wherein the adverse outcomes are due to uncertainties during deployment of at least one surgical device.

5. The computer implemented method of claim 1, further comprising displaying the decision tree in real time when there is new data added to the patient's EMR.

6. The computer implemented method of claim 1, wherein the medical images comprise X-ray images and/or computer generated tomography images.

7. The computer implemented method of claim 3, wherein the pre-calculated probability distribution functions are conditioned on at least one of the patient's demographic data, morbid symptoms, vital signs, medications, surgery history, family medical history, genetic data, laboratory test data, diseases records, allergies, hospital, and geographic region.

8. The computer implemented method of claim 3, wherein the pre-calculated probability distribution functions are conditioned on at least one of a selection of at least one valve for the at least one surgical treatment or intervention, geographic location, age of the patient at time of the at least one surgical treatment or intervention, and co-morbidities of the patient.

9. The computer implemented method of claim 3, wherein the pre-calculated probability distribution functions are conditioned on each of the adverse outcomes due to one or more of root rupture, paravalvular leakage level, patient prosthesis mismatch, valve thrombosis, coronary obstruction, valve embolization, placement of permanent pacemaker, stroke, patient prosthesis mismatch, and valve thrombosis.

10. The computer implemented method of claim 5, further comprising retrieving the new data from a wearable device, wherein the data comprises biological, physiological, cognitive, mental, and/or biomarker data of the patient.

11. A system for prescribing optimal treatment paths, comprising:

at least one memory comprising instructions; and at least one processor configured to execute the instructions, which, when executed, cause the at least one processor to:

retrieve data relevant to a diagnosis of a disease, the data comprising a patient's updated electronic medical record (EMR) comprising medical images and at least one of: the patient's demographic data, morbid symptoms, vital signs, medications, surgery history, family medical history, genetic data, laboratory test data, diseases records, and allergies;

identify treatment path options based on selections made by medical professional personnel or according to guidelines generated by medical societies, wherein the treatment path options comprise at least one surgical treatment or intervention;

use a trained predictive life-expectancy model to predict a life expectancy for each of the treatment path options based on the data and probability distribution functions conditioned on adverse outcomes of the at least one surgical treatment or intervention, wherein the adverse outcomes are generated by predictive models comprising a biomechanical model based on the medical images;

perform Monte-Carlo simulations using the probability distribution functions of the adverse outcomes to calculate a total probability function of the life expectancy for each of the treatment path options; and interactively display a decision tree to the medical professional personnel and the patient, the decision tree comprising the treatment path options and corresponding total probability functions of the life expectancies, present real time predicted life expectancies, sort the life expectancies from a maximum probability to a minimum probability, and present the life expectancies and temporal and monetary costs for each of the treatment path options.

12. The system of claim 11, wherein the predictive models further comprise one or more of a trained artificial neural net model, a statistical model, a reduced order model, a semi-empirical, and an empirical model.

13. The system of claim 11, wherein the probability distribution functions comprise individual probabilities of each of the adverse outcomes and pre-calculated probability distribution functions of life expectancy after each of the at least one surgical treatment or intervention.

14. The system of claim 11, wherein the adverse outcomes are due to uncertainties during deployment of at least one surgical device.

15. The system of claim 11, wherein the instructions, which, when executed, cause the at least one processor to display the decision tree in real time when there is new data added to the patient's EMR.

16. The system of claim 11, wherein the medical images comprise X-ray images and/or computer generated tomography images.

17. The system of claim 13, wherein the pre-calculated probability distribution functions are conditioned on at least one of the patient's demographic data, morbid symptoms, vital signs, medications, surgery history, family medical history, genetic data, laboratory test data, diseases records, allergies, hospital, and geographic region.

18. The system of claim 13, wherein the pre-calculated probability distribution functions are conditioned on at least one of a selection of at least one valve for the at least one surgical treatment or intervention, geographic location, age of the patient at time of the at least one surgical treatment or intervention, and co-morbidities of the patient.

19. The system of claim 13, wherein the pre-calculated probability distribution functions are conditioned on each of the adverse outcomes due to one or more of root rupture, paravalvular leakage level, patient prosthesis mismatch, valve thrombosis, coronary obstruction, valve embolization, placement of permanent pacemaker, stroke, patient prosthesis mismatch, and valve thrombosis.

20. The system of claim 15, wherein the instructions, which, when executed, cause the at least one processor to retrieve the new data from a wearable device, wherein the data comprises biological, physiological, cognitive, mental, and/or biomarker data of the patient.

\* \* \* \* \*